United States Patent
Xu et al.

(10) Patent No.: US 10,198,557 B2
(45) Date of Patent: Feb. 5, 2019

(54) SYSTEM AND METHOD FOR CONTENT-BASED MEDICAL MACRO SORTING AND SEARCH SYSTEM

(71) Applicant: KONINKLIJKE PHILIPS N.V., Eindhoven (NL)

(72) Inventors: Ye Xu, Milford, CT (US); Yuechen Qian, Briarcliff Manor, NY (US)

(73) Assignee: Koninklijke Philips N.V., Eindhoven (NL)

( * ) Notice: Subject to any disclaimer, the term of this patent is extended or adjusted under 35 U.S.C. 154(b) by 298 days.

(21) Appl. No.: 15/022,694

(22) PCT Filed: Sep. 22, 2014

(86) PCT No.: PCT/IB2014/064723
§ 371 (c)(1),
(2) Date: Mar. 17, 2016

(87) PCT Pub. No.: WO2015/044852
PCT Pub. Date: Apr. 2, 2015

(65) Prior Publication Data
US 2016/0232329 A1    Aug. 11, 2016

Related U.S. Application Data

(60) Provisional application No. 61/884,158, filed on Sep. 30, 2013.

(51) Int. Cl.
*G06F 19/00* (2018.01)
*G06F 17/24* (2006.01)
(Continued)

(52) U.S. Cl.
CPC ........ *G06F 19/3487* (2013.01); *G06F 17/248* (2013.01); *G06F 17/30321* (2013.01);
(Continued)

(58) Field of Classification Search
CPC combination set(s) only.
See application file for complete search history.

(56) References Cited

U.S. PATENT DOCUMENTS

| | | |
|---|---|---|
| 8,046,226 B2 | 10/2011 | Soble et al. |
| 8,165,878 B2 | 4/2012 | Roberge et al. |

(Continued)

FOREIGN PATENT DOCUMENTS

CN    101297351 A    10/2008

*Primary Examiner* — Maroun P Kanaan

(57) ABSTRACT

When automatically populating medical report templates, insertable macros are indexed and searched not only my name or title but also by contents, such as keywords times, pre-defined terms for key information included in the macro, free texts in the macros, etc. When a unique macro is found, the system inserts the text of the macro into the report being generated. If multiple related macros are found, the system highlights the macros for user review. After the insertion of the macro into the template, the system identifies pre-defined terms and fills in the key information value(s). The system thus facilitates, e.g., radiologists' observation reporting procedure through an intelligent matching algorithm that facilitates finding a unique macro, which in turn aids in filling in report field instance values and optimizes radiology workflow.

15 Claims, 4 Drawing Sheets

(51) Int. Cl.
*G06F 17/30* (2006.01)
*G10L 15/26* (2006.01)
*G16H 15/00* (2018.01)

(52) U.S. Cl.
CPC .. *G06F 17/30424* (2013.01); *G06F 17/30752* (2013.01); *G06F 19/32* (2013.01); *G10L 15/265* (2013.01); *G16H 15/00* (2018.01)

(56) References Cited

U.S. PATENT DOCUMENTS

| | | |
|---|---|---|
| 2002/0082825 A1 | 6/2002 | Rowlandson et al. |
| 2009/0187407 A1 | 7/2009 | Soble et al. |
| 2011/0264652 A1* | 10/2011 | Roberge ................ G10L 15/08 707/723 |
| 2012/0035963 A1 | 2/2012 | Qian et al. |
| 2012/0191453 A1 | 7/2012 | Roberge et al. |
| 2013/0151286 A1 | 6/2013 | Kablotsky et al. |

* cited by examiner

SYSTEM AND METHOD FOR CONTENT-BASED MEDICAL MACRO SORTING AND SEARCH SYSTEM

CROSS-REFERENCE TO PRIOR APPLICATIONS

This application is the U.S. National Phase application under 35 U.S.C. § 371 of International Application No. PCT/IB2014/064723, filed on Sep. 22, 2014, which claims the benefit of U.S. Provisional Application No. 61/884,158, filed on Sep. 30, 2013. These applications are hereby incorporated by reference herein.

The present application finds particular application in medical report generation systems. However, it will be appreciated that the described techniques may also find application in other report generation systems, other medical scenarios, or other sorting techniques.

In conventional radiology reading workflows, after loading medical images, radiologists need to review images and interpret them to generate a report for diagnosis or recommendation. Reports are important resources for radiologists to record a patient's disease observations as well as to review a patient's history before reading images. Increasingly, radiologists prefer to concentrate on the screen and use a hands-free tool, such as a speech microphone, to dictate the key findings during the reporting phase, addressing as well the problem of occupational stress and fatigue. Furthermore, the macro is an important feature typically used with dictation or typing to speed up the reporting and editing process in computer applications.

Currently, macros are only pure free texts and can only be searched by name. Key pieces of information can be used to select from a list of standard medical terms; for example, prostate can be replaced with kidney, spleen and uterus, etc. Users can select one from the options to describe a finding observed at a given anatomy. In this way, users can reuse macros through different combinations of values. However, conventional approaches do not facilitate efficiently finding a unique macro or template from hundreds of available macros through typing or speech of key words, and, when desired, filling in and editing some key pieces of information (words, phrases) in the macro. In order to find a unique macro, the typical approach is to search using the free text in the name or title of a macro. Typically, radiologists only use simple narrative macros. When searching for macros, conventional algorithms employ text matching using only the macro's names, thus potentially returning multiple macros; many are unrelated to the current exam.

The present application relates to new and improved systems and methods that facilitate providing a content-based approach to indexing and searching medical macros for populating medical record templates, which overcome the above-referenced problems and others.

In accordance with one aspect, a system that facilitates content based sorting and searching of medical macros for populating medical report templates comprises a user interface by which a user enters one or more words, and a preprocessing module that analyzes the user entered words and generates a query comprising keywords generated from the user entered words. The system further comprises a matching module that compares the query to a plurality of preprocessed macros, generates a candidate macro list comprising macros having at least one word in common with the query, and identifies a unique macro for insertion into the medical template. The unique macro comprises a minimum number of words, and a maximum number words in common with the query, relative to other candidate macros.

According to another aspect, a method of sorting and searching of medical macros for populating medical report templates comprises receiving user input text, analyzing the user input text, generating a query comprising keywords generated from the user input text, and comparing the query to a plurality of preprocessed macros. The method further comprises generating a candidate macro list comprising macros having at least one word in common with the query, and identifying a unique macro for insertion into the medical template. The unique macro comprises a minimum number of words, and a maximum number words in common with the query, relative to other candidate macros.

According to another aspect, a method of identifying unique macro from a set of macros using a sequential shortest word matching algorithm comprises receiving user input words, and preprocessing the received user input words by truncating the received input words until each of the received input words is represented by its stem, removing redundant words, and removing stop words. The method further comprises identifying in the set of macros a plurality of macros that have at least one word in common with the preprocessed user input words, and identifying a unique macro for insertion into a medical template, wherein the unique macro comprises a minimum number of words, and a maximum number of words in common with the preprocessed user input words, relative to other macros in the plurality of macros.

On advantage is that macros are indexed and searched by content rather than only be name or title.

Another advantage is that medical report generation time is reduced.

Still further advantages of the subject innovation will be appreciated by those of ordinary skill in the art upon reading and understanding the following detailed description.

The innovation may take form in various components and arrangements of components, and in various steps and arrangements of steps. The drawings are only for purposes of illustrating various aspects and are not to be construed as limiting the invention.

The subject innovation overcomes the aforementioned problems by providing systems and methods that can search a macro based on, in addition to macro name, the contents of the macro including all key information, pre-defined terms for the key information, and free texts in the macros, etc. When a unique macro is found, the system inserts the text of the macro into the report being generated. If multiple related macros are found, the system highlights the macros for user review. After the insertion of the macro into a report template, the system identifies a pre-defined term and fills in the key information value(s) in the macro. The system thus facilitates radiologists' observation reporting procedure through an intelligent matching algorithm to find a unique matching macro, which aids in filling in report field instance values and optimizes radiology workflow.

"Macros" as used herein denote pieces of pre-defined text that can be inserted into a report. The text in macros describes medical terms, findings/observations, properties of observations, and diagnosis, usually a full sentence. Macros can facilitate radiologists' observation reporting procedure, decrease ambiguity, assure completeness and consistency, expose best practices, and, furthermore, optimize radiology workflow.

Figure 1:
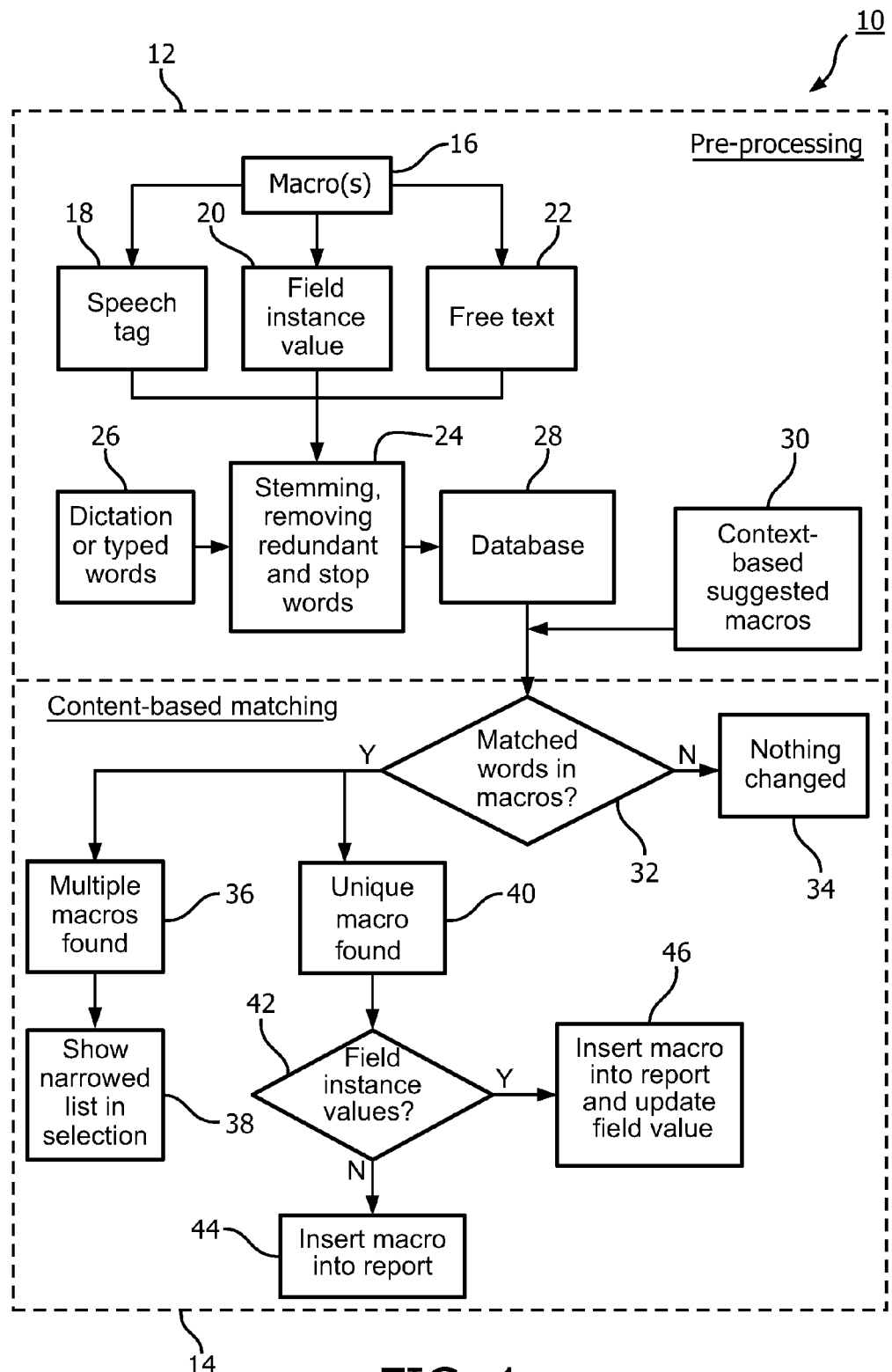
FIG. 1 illustrates an architecture that facilitates indexing macro contents and automatically identifying a unique macro by inputting one or more key words and automatically filling in pre-defined values in fillable fields in a medical report template.

FIG. 1 illustrates an architecture 10 that facilitates indexing macro contents and automatically identifying a unique macro by inputting (e.g., typing or saying, etc.) one or more key words (e.g., key information in the pre-defined texts for the macro) and automatically filling in pre-defined values in fillable fields in a report template to improve radiologists' workflow. The architecture 10 includes a preprocessing module 12 and a content-based matching module 14. During preprocessing, macros 16 are preprocessed to modify the macros by appending speech tags 18, field instance values 20, and free text 22 thereto, and the modified macros are input into a stemming module 24 that truncates key words to their respective stems, removes redundant words and stop words from the macro. Also input into the stemming module are dictated and/or typed words 26, which are also stemmed by the stemming module. The stemming module 24 also removes redundant words and stop words from the dictated and/or typed words 26. The preprocessed content-based macros output from the stemming module are then stored in the database 28, along with one or more queries generated from the preprocessed input words. The preprocessing module 12 also comprises a context-based suggested macro module 30 that suggests context-based macros.

During the content-based matching phase, a comparator module 32 receives preprocessed macros from the database 28 as well as context-based suggested macros from the suggested macro module 30 and determines whether the preprocessed macros and the suggested macros common or matching words. If not, then at 34 nothing is changed. The comparator module 32 may use for example sequential shortest word matching algorithm, the three-part content-based matching algorithm (e.g. using speech tags, field instance values, and free texts), or any other suitable matching algorithm. If a determination is made by the comparator module 32 the context-based suggested macro and the content-based macro retrieved from the database 28 have at least one common word, and if multiple macros are found having common words at 36, then at 38 a macro list is presented to the user. If a unique macro is found at 40 based on the determination made by the comparator module 32, at 42 a determination is made regarding whether any field instance values are needed to fill the macro. If not, then at 44 the macro is inserted into the report template being filled. If field instance values are needed to fill the macro as determined at 42, then at 46 the macros inserted into the report template being filled and the field value is updated. The above-described approach to indexing involves generating content key words for each macro, which are used to search macros. This approach can employ Natural Language Processing (NLP) technology or a technique to generate semantic words such as is described as follows.

The following example illustrates how a macro is indexed and stored, e.g. during the preprocessing phase. The following macro definition employs a markup language which consists of three parts: speech tag, key information (e.g. field instance value) and free text. The speech tag is the general dictated tag name used to retrieve a given macro (in this example, "cystic mass"). Free texts are the static portion of the content in a macro. For instance:

```
<Macro Key="CysticMass" Name="Cystic mass"
    SpeechTag="cystic mass" Anatomy="prostate"
    FindingType="Mass">
    <FreeText>A complex cystic mass measuring </FreeText>
        <FieldInstance Key="Measurement" Name="Measurement"
    SpeechTag="measurement"/>
        <FreeText> is present in the [Anatomy] </FreeText>
        <FreeText> suspicious for an abscess. </FreeText>
    </Macro>
```

"Anatomy" here is the key information of the macro. In this example, using existing ontology tools, or manually pre-defined terms of anatomy, in this example "Anatomy" can be replaced with four options: kidney, prostate, spleen, and uterus.

Before the three parts are saved into the database, a pre-processing step is performed, during which stemming and stop word removal logic is applied. The stemming module 24 identifies the root form of the words, such as "enhancing" or "enhanced," which can be stemmed to "enhanc", etc. It will be noted that in the described approach, the root does not have to exist as a complete, real word. Stop words include some articles, conjunctions, etc., such as "there, is, the, an, with, and, of", without being limited thereto. After the pre-processing phase, the description of the above macro "cystic mass" becomes "cystic mass complex kidne prostat spleen uteru abscess", which represent the indexing terms of the macro that are used for content-based searching. However, before the content-based search algorithm is applied, it is preceded by a step that reduces the list of initial macros to a limited subset of macros, wherein the list is filtered using the context of the patient's DICOM (Digital Imaging and Communications in Medicine) image information.

Figure 2:
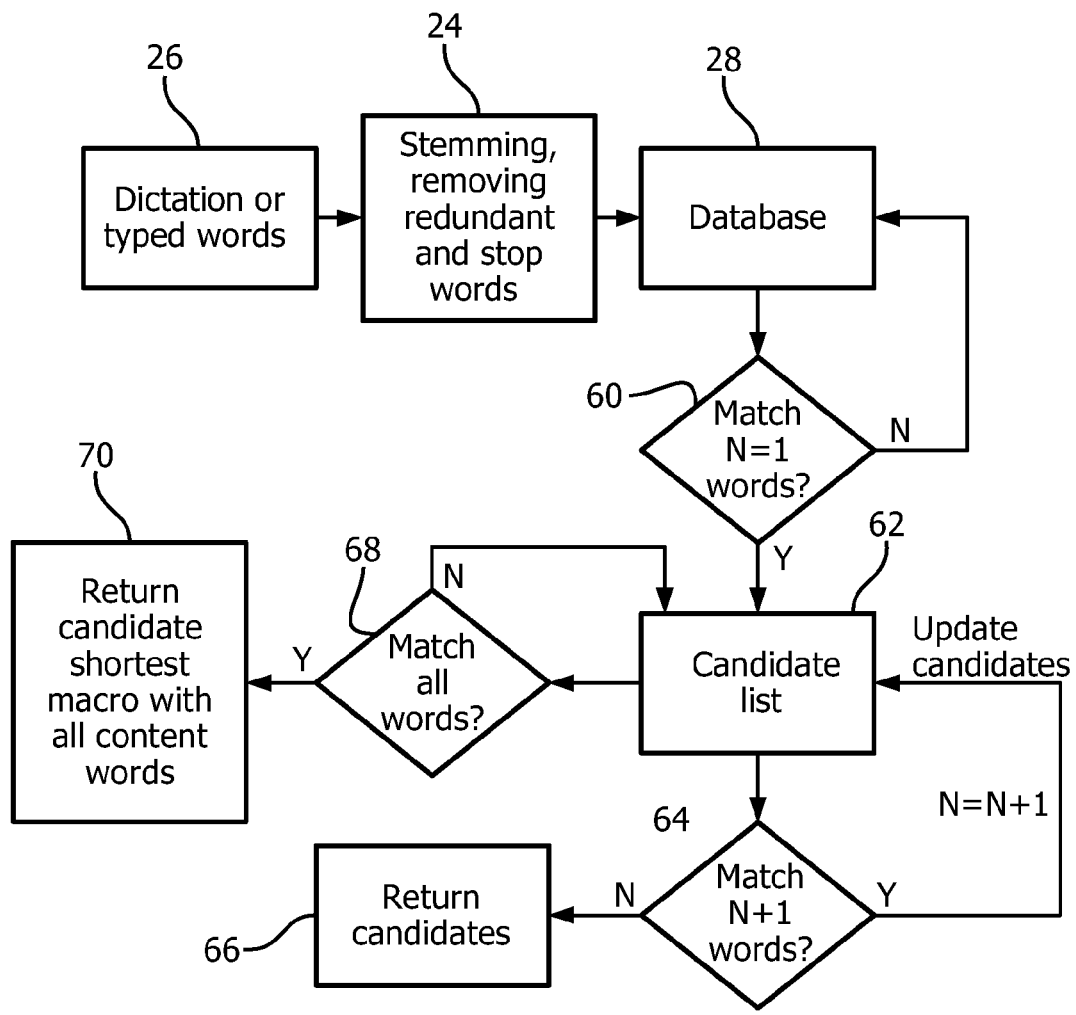
FIG. 2 illustrates a method for performing a sequential shortest word matching algorithm to identify a unique macro.

With continued reference to FIG. 1, FIG. 2 illustrates a method for performing a sequential shortest word matching algorithm to identify a unique macro. The matching algorithm is employed to identify a unique macro or related macros with the fewest number of content words, but with the maximum number of matching words. The unique macro is the macro with the smallest number of content words among multiple macros containing matching words. The greater the number of words in the macro, the greater the chance the theme of the macro is divergent even though it contains the same key words. Thus, the algorithm searches for candidates of related macros, and updates the pool of candidates with the increased number of words matched, until it has identified a macro that matches all the searching words and has the smallest number of words, otherwise the algorithm returns related macros with the maximum number of matching words.

According to FIG. 2, dictated or typed user input words 26 are stemmed and preprocessed to remove redundant words, stop words, etc., and the content-based preprocessed macros are stored in the database 28, as set forth the preprocessing steps of FIG. 1. At 60, a determination is made regarding whether N words in a content-based macro match words in the preprocessed user input words, where N is initialized to 1. If not the method returns to the database 28 to retrieve a subsequent content-based macro. If the content-based macro(s) and the user input words have a word in common, then a macro candidate list is generated at 62. At 64, a determination is made regarding whether any macro in the candidate list is two words in common with the user input words. If not, at 66 the candidate list is returned presented to the user. If one or more candidate macros has two words in common with the user input words, then N is incremented (e.g. to 3 and so on) and the method reverts to 62 where the candidate list is updated. Concurrently or periodically a determination is made, at 68, whether all words in a given candidate macro are common to the user input words. If not, then the method reverts to 62. If so, at 70 a shortest candidate macro having all content words (i.e. the unique macro) is returned presented to the user.

After identifying a unique macro the algorithm uses knowledge of the different fields attached to the unique macro and automatically recognizes fields and their values when mentioned as speech-based inputs. For example, if the user says "anatomy spleen", the system identifies the field name and the field instance value and populates the "anatomy" field with the value "spleen". In another example, the user can simply say "spleen", and the algorithm identifies the field which has that value as one of its pre-set list of values (in this case, Anatomy: spleen) and updates its value to "spleen". In another example, if the user says "measurement 1.6", the "measurement" field is updated with the user-provided value, which is the number after the word "measurement" (in this case, "1.6").

According to another example, if the command "Macro cystic mass kidney" is spoken or typed as input words, the system initiates a search for a unique matching macro, and generates a query vector comprising the words "cystic mass kidne" for this command. The system then compares the query vector with multiple vectors of macros in the database. The macro in the database that has the fewest words in its vector, but with the maximum number of words in common with the query vector (relative to other macros), is identified as the unique macro. At this point, pre-defined text for the macro is inserted into a report template and the "Anatomy" key information is replaced with e.g. "Kidney" in the macro. It will be appreciated that the described searching and indexing algorithm can also be applied as a template searching algorithm.

The macro below is an example to describe a pre-defined text for the macro "cystic mass prostate", which would be inserted under the "Finding" section.

A complex cystic mass measuring [ ] in mm is present in the prostate.

The foregoing is a "semantic" macro, which is a structured macro where some of the terms contained pre-defined types of content, as shown in the example below where the square brackets signify the different pre-defined terms.

A complex cystic mass measuring [measurement] in mm is present in the [Anatomy].

The part of the above macro "Anatomy" has field instance values to describe the field in the macro. For this field, users can have several options to select from. For example, "Anatomy" can have several value options such as kidney, prostate, spleen or uterus. Users select one option to describe a finding observed at a given anatomical location. In this manner, users can reuse macros through different combinations of field instance values.

The following example illustrates how a structured macro is indexed. The following macro definition employs a markup language which consists of three parts: speech tag, field instance and free text. Speech tag is "name" to retrieve this macro (in this example, it is "cystic mass"). Free texts are the static portion of the content in a macro.

```
<Macro Key="CysticMass" Name="Cystic mass"
SpeechTag="cystic mass" Anatomy="FieldInstance:Anatomy"
FindingType="Mass" FindingCode="http://www.radlex.org/RID/
RID3874">
<FreeText>A complex cystic mass measuring </FreeText>
<FieldInstance Key="Measurement" Name="Measurement"
SpeechTag="measurement"/>
<FreeText> is present in the </FreeText>
<FieldInstance Key="OrganEnlargement.Anatomy" Name="Anatomy"
SpeechTag="anatomy"/>
<FreeText> suspicious for an abscess. </FreeText>
</Macro>
```

The field instance above indicates the location where semantic field values are held. For example, the field instance "Anatomy" refers to the field value set "OrganEnlargement.Anatomy", which could be defined as follows:

```
<Field Key="OrganEnlargement.Anatomy" ValueType="enum">
    <Option Value="kidney" />
    <Option Value="prostate" />
    <Option Value="spleen" />
    <Option Value="uterus" />
</Field>
```

The herein described systems and methods thus facilitate performing preprocessing, context-based pre-filtering to suggest macros, and content-based matching with patient data to identify and retrieve the most relevant macro. The preprocessing module 12 stores macros in the database 28 in a structure which facilitates searching and editing. The context-based filtering uses the DICOM information of a current image study to narrow the list of macros. Content-based matching is then performed to find an appropriate macro.

Figure 3:
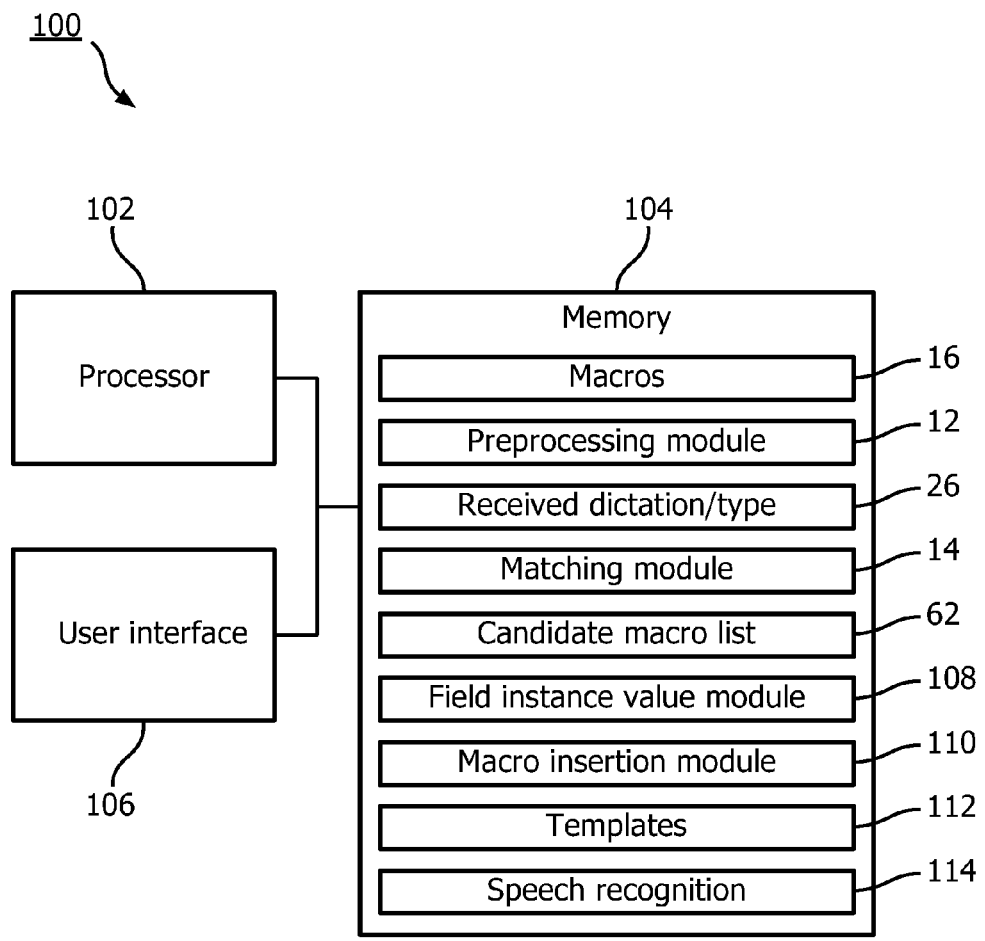
FIG. 3 illustrates a system that facilitates content-based sorting and searching of macros for use in filling out medical reports and the like, in accordance with one or more aspects described herein.

FIG. 3 illustrates a system 100 that facilitates content-based sorting and searching of macros for use in filling out medical reports and the like, in accordance with one or more aspects described herein. The system includes a processor 102 operably coupled to a memory 104 and a user interface 106. The processor 102 executes, and the memory 104 stores, computer-executable instructions (e.g., routines, programs, algorithms, software code, etc.) for performing the various functions, methods, procedures, etc., described herein. Additionally, "module," as used herein, denotes a set of computer-executable instructions, software code, program, routine, or other computer-executable means for performing the described function, or the like, as will be understood by those of skill in the art.

The memory may be a computer-readable medium on which a control program is stored, such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor can read and execute. In this context, the systems described herein may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphical card CPU (GPU), or PAL, or the like.

The memory stores a plurality of macros 16 which are indexed based on their contents by preprocessing module 12 (see e.g. FIG. 1). The preprocessing module 12 analyzes user inputs including received dictation and/or type 26 received via the user interface 106 and generates queries to look up macros. The processor executes, and the memory stores the matching module 14 (see e.g. FIG. 1) to search macros based on a query generated by the preprocessing module 12. The matching module 14 generates a candidate macro list 62 from which a unique macro is identified, as described with regard to FIGS. 1 and 2. Also stored in the memory and executed by the processor is a field instance value module 108 that automatically identifies a field of a matching macro to which a part of the input text 26 belongs, and inserts the text and the identified field. Once the unique macro has been populated with the identified field instance value, a macro insertion module 110 inserts the populated macro into a report template 112 which is then presented to the user via the user interface 106. In one example, the user interface 106 presents the pre-defined texts of an inserted macro into the relevant section of the template, and highlights the modifiable fields in the macro for review by the user.

The memory also stores a speech recognition module 114 that is executed by the processor to perform speech recognition and voice data received from the user via the user interface 106. According to one or more features described herein speech recognition is used to recognize navigational voice commands. For example, the system starts in the "Wait" state and switches modes as commands are received through the user interface. For instance, if the command starts with "Macro", the system is in a state of "Macro", and waits for key words to search for a macro. To further this example, in the speech command "Macro cystic mass prostate", the keys words are "cystic mass prostate". If the system cannot find a related macro, it remains in the "Macro" state, waiting for new key words. The same logic can be applied to a "Template" command by which templates are sorted and searched in the manner described herein with regard to macros.

Commands can also be provided to insert field instance values. For example, after selecting a macro, if the user says "anatomy liver", the system populates the "anatomy" field with the value "liver". A keyboard input shifts the system into the free text editor state. At that time, any typed input is inserted into the report area. The system can also link a bookmark (an observation on the image) to a macro by saying "Add bookmark 5", which creates a persistent link between image bookmark #5 in the current exam and the current selected macro in the report area. Users can update an existing macro by changing field values in the macro (pronouncing first the field name, followed by its field instance value). Navigational voice commands are also provided for macro management. For example, commands are also supplied to filter the macros by anatomy, show all macros, and navigate different sections in the report.

Figure 4:
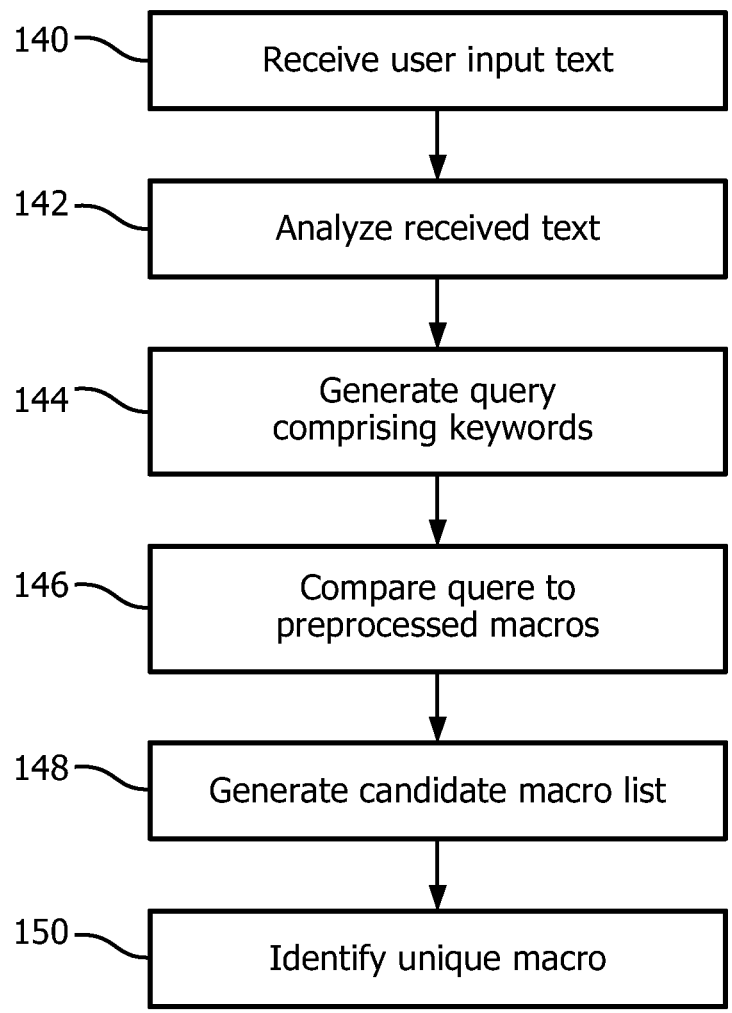
FIG. 4 illustrates a method for sorting and searching of medical macros for populating medical report templates, in accordance with one or more aspects described herein.

FIG. 4 illustrates a method for sorting and searching of medical macros for populating medical report templates, in accordance with one or more aspects described herein. At 140, user input text is received. In the text may be typed, voice data (e.g. dictated), etc. At 142, the user input text is analyzed to identify words stems for words included in the input text and the like. At 144, a query is generated comprising keywords stems identified in the user input text. At 146, the query is compared to a plurality of preprocessed macros. The preprocessed macros have also been stemmed to reduce keywords to their respective stems, as well as having redundant words and stop words removed. At 148, a candidate macro list is generated comprising macros having at least one word or word stem in common with the query. At 150, a unique macro is identified for insertion into the medical template. The unique macro comprises a minimum number of words relative to other candidate macros, and a maximum number words in common with the query relative to other candidate macros.

In one embodiment, a plurality of macros is indexed as a function of the contents of the macros, for example by appending one or more of speech tags, field instance values, and free texts to the macros as described with regard to the preceding figures. One or more modifiable fields within a matching macro can be identified for insertion of at least a portion of the input text, and the input text can be inserted in the identified field(s) to populate the macro, which is then presented to the user via a user interface. Additionally or alternatively, pre-defined texts of a macro can be inserted into the relevant section of the medical template, and one or more modifiable fields in the macro can be highlighted for review by the user. In another embodiment speech recognition is employed to analyze voice data received from the user via a user interface and to provide input words recognized in the voice data for preprocessing.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the invention is now claimed to be:

1. A system for facilitating content based sorting and searching of medical macros for populating medical report templates, including:
   a user interface by which a user can enter one or more words; and
   one or more processors configured to execute:
      a preprocessing module that is adapted to analyze the user entered words and to generate a query comprising keywords generated from the user entered words; and
      a matching module that is adapted to compare the query to a plurality of preprocessed macros, to generate a candidate macro list comprising candidate macros having at least one word in common with the query, and to identify a unique macro for insertion into the medical template;
   wherein the unique macro comprises a minimum number of total words, and a maximum number of words in common with the query, relative to other candidate macros;
   wherein when identifying the unique macro, the matching module is further configured to search for candidate macros and update the candidate macro list as candidate macros having an increased number of words matched to the query are identified, until the matching module identifies the unique macro comprises a maximum number of keywords relative to other candidate macros and has a smallest total number of words relative to other candidate macros;
   wherein the number of words matched to the query is prioritized as a criteria over the total number of words in the candidate macro when identifying the unique macro.

2. The system according to claim 1, further comprising a database that is adapted to store a plurality of macros which are indexed based on their contents by the preprocessing module.

3. The system according to claim 2, wherein the preprocessing module is adapted to index the macros by appending one or more of speech tags, field instance values, and free texts to the macros, wherein a speech tag is a generally input name used in retrieving a macro.

4. The system according to claim 1, further comprising a field instance value module that is adapted to automatically identify a field of a matching macro to which at least a portion of the input text belongs, and to insert the portion of input text in the identified field to populate the macro.

5. The system according to claim 4, further comprising a macro insertion module that adapted to insert the populated macro into a report template that is to be presented to the user via the user interface.

6. The system according to claim 5, wherein the user interface is adapted to insert pre-defined texts of an inserted macro into the relevant section of the medical template, and to highlight one or more modifiable fields in the macro for review by the user.

7. The system according to claim 1, further comprising a speech recognition module that is adapted to analyze voice data received from the user via the user interface and to provide input words to the preprocessing module.

8. A method of sorting and searching of medical macros for populating medical report templates, including:
receiving user input text;
analyzing the user input text;
generating a query comprising keywords generated from the user input text;
comparing the query to a plurality of preprocessed macros;
generating a candidate macro list comprising candidate macros having at least one word in common with the query; and
identifying a unique macro for insertion into the medical template by searching for candidate macros and updating the candidate macro list as candidate macros having an increased number of words matched to the query are identified, until the unique macro is identified as comprising a maximum number of keywords relative to other candidate macros and a smallest total number of words relative to other candidate macros, wherein the number of words matched to the query is prioritized as a criteria over the total number of words in the candidate macro when identifying the unique macro;
wherein the unique macro comprises a minimum total number of words, and a maximum number of words in common with the query, relative to other candidate macros.

9. The method according to claim 8, further comprising indexing a plurality of macros as a function of the contents of the macros.

10. The method according to claim 9, wherein indexing the macros further comprises appending one or more of speech tags, field instance values, and free texts to the macros, wherein a speech tag is a generally input name used in retrieving a macro.

11. The method according to claim 8, further comprising automatically identifying a field of a matching macro to which at least a portion of the input text belongs, and inserting the portion of input text in the identified field to populate the macro.

12. The method according to claim 11, further comprising inserting the populated macro into a medical report template that is presented to the user via a user interface.

13. The method according to claim 12, further comprising inserting pre-defined texts of an inserted macro into the relevant section of the medical template, and highlighting one or more modifiable fields in the macro for review by the user.

14. The method according to claim 8, further comprising analyzing voice data received from the user via a user interface and providing input words recognized in the voice data to a preprocessing module for preprocessing.

15. A processor or computer-readable medium carrying a computer program that controls one or more processors to perform the method of claim 8.

* * * * *